(12) United States Patent
Johansson

(10) Patent No.: US 7,846,357 B2
(45) Date of Patent: Dec. 7, 2010

(54) METHOD AND ARRANGEMENT FOR SUPPLYING A DENTAL PRODUCT

(75) Inventor: Ulf Johansson, Onsala (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 608 days.

(21) Appl. No.: 11/574,387

(22) PCT Filed: Aug. 11, 2005

(86) PCT No.: PCT/SE2005/001200

§ 371 (c)(1),
(2), (4) Date: Nov. 9, 2007

(87) PCT Pub. No.: WO2006/025776

PCT Pub. Date: Mar. 9, 2006

(65) Prior Publication Data

US 2009/0267251 A1 Oct. 29, 2009

(30) Foreign Application Priority Data

Sep. 1, 2004 (SE) .................................. 0402109

(51) Int. Cl.
*A61C 13/00* (2006.01)
(52) U.S. Cl. ....................................................... 264/16
(58) Field of Classification Search ................... 264/16; 433/51
See application file for complete search history.

(56) References Cited

U.S. PATENT DOCUMENTS 4,615,678 A * 10/1986 Moermann et al. ......... 433/201.1
5,939,211 A * 8/1999 Mormann ................. 428/542.8
2002/0125619 A1 9/2002 Bodenmiller et al.
2002/0137002 A1* 9/2002 Bodenmiller ................. 433/51
2003/0031977 A1* 2/2003 Bodenmiller et al. ......... 433/49
2003/0132539 A1* 7/2003 Althoff et al. ................. 264/16
2004/0072121 A1* 4/2004 Filser et al. .................... 433/25
2007/0108645 A1* 5/2007 Von Schroeter et al. ....... 264/16

FOREIGN PATENT DOCUMENTS

WO    WO 02/45614 A1    6/2002

OTHER PUBLICATIONS

International Search Report for Application No. PCT/SE2005/001200 (the PCT counterpart of the parent application).

* cited by examiner

*Primary Examiner*—Joseph S Del Sole
*Assistant Examiner*—Kimberly A Stewart
(74) *Attorney, Agent, or Firm*—Knobbe Martens Olson & Bear, LLP

(57) ABSTRACT

An arrangement and method are provided for supplying material to production equipment for ceramic products. The arrangement comprises a first unit that can be at least partially surrounded by a second unit to which it is secured via its outer surface. The second unit can be designed so that it can be fed forward and divided by the production equipment. The first and second units can be arranged to facilitate silhouetting in at least the first unit and to facilitate the creation of at least one securing part between the first and second units. The securing part can comprise one of a combination of the material of the second unit with a joining material and a combination of the material of the first unit with the joining material.

16 Claims, 2 Drawing Sheets

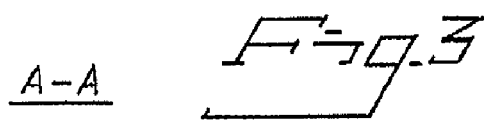
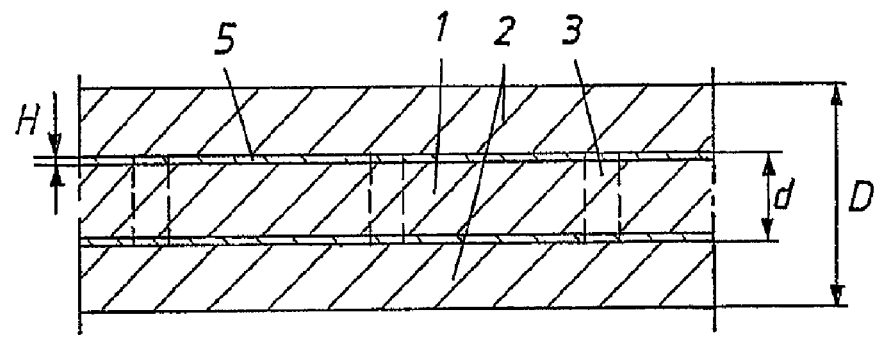
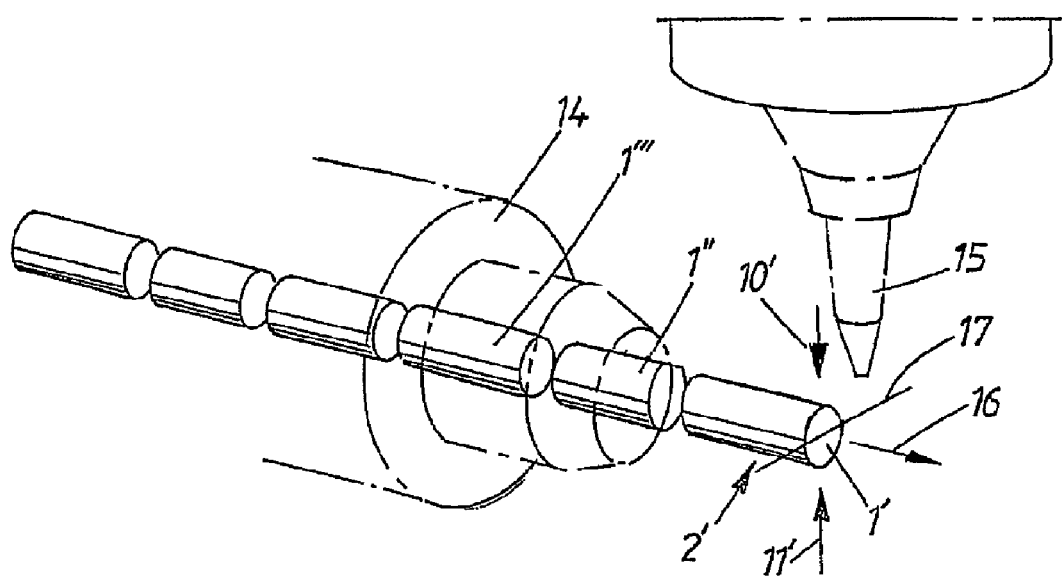

METHOD AND ARRANGEMENT FOR SUPPLYING A DENTAL PRODUCT

CROSS-REFERENCE TO RELATED APPLICATIONS

This application is a U.S. National Phase of International Application No. PCT/SE2005/001200, filed Aug. 11, 2005, which claims priority to Swedish Patent Application No. 0402109-3, filed Sep. 1, 2004, each of which is hereby incorporated by reference in its entirety.

BACKGROUND

1. Field of the Inventions

The present inventions relate to a method for supplying a product that can be used for production of a dental prosthesis and which can be configured with a silhouetted, unsintered or presintered first unit of ceramic material and a second unit retaining the latter via securing parts. The inventions also relate to an arrangement for supplying a product that can be used for production of a dental prosthesis and can have a silhouetted first unit made of unsintered or presintered ceramic material and, arranged outside the latter, a second unit for holding the first unit by means of securing parts that can extend between the units. The inventions also relate to an arrangement for supplying unsintered or presintered material to production equipment for ceramic or ceramic products.

2. Description of the Related Art

In the production of dental products made of ceramic material, it is known to make the product in question from an unsintered or presintered material (raw material, blank). The material in the unsintered or presintered state is relatively fragile and therefore difficult to transport, handle and machine. The material is additionally quite expensive, which means that damage to components has to be avoided.

Various measures have therefore been proposed to facilitate the handling and machining of the material in question, and in this connection reference may be made, inter alia, to PCT Application WO 02/45614, entitled Holding Device for a Ceramic Blank, to Filser et al., which has proposed a holding arrangement for the material during the machining.

SUMMARY

An aspect of at least one of the embodiments disclosed herein includes the realization that there is a need in the art for methods and arrangements that can further reduce the risk of damage to the ceramic products during normal handling and that can thereby mitigate the loss of expensive material, which in turn simplifies the production procedure as such and reduces the costs. There is also a need in the art for an improved and more efficient production process for dental products such as dental bridges, individual teeth, etc. For example, advantageous production installations can be set up to avoid costly robotic charging. An object of at least one of the embodiments disclosed herein is to solve all or some of these problems.

In accordance with an embodiment, a method is provided for production of a dental prosthesis using a product comprising a first unit and a second unit being secured to the first unit via at least one securing part. The first unit, which can be made of a ceramic material, can be at least partially enclosed within and anchored to the second or enclosure unit. The first unit can be joined to the second unit by means of joining material, such as glue. The joining material can be positioned on an outer surface of the first unit and an inner surface of the second unit.

The method can further comprise performing a silhouetting process, preferably milling, at a transition between the materials. The silhouetting process can be carried out from two opposite directions. Further, in the silhouetting process, outer and inner silhouettes can be formed on the respective ones of the first and second units to face one another. In addition, the securing part can be formed to extend between the inner and outer silhouettes. The securing part or section can be made of one or a combination of the materials of the first unit, the second unit, and the joining material. Thus, in accordance with an embodiment, the first unit can be formed by a ceramic material defined by the outer silhouette, and the second unit can be formed at least partially by surrounding material defined by the internal silhouette.

In a preferred embodiment, the second unit can be a tubular unit. The second unit can be preferably made of aluminum, a dimensionally stable plastic material, or an equivalent material that is preferably relatively inexpensive compared to the ceramic material. A surface of the first unit can be attached to the inner surface of the second unit by means of glue or an adhesive connection. In some embodiments, the first unit can be a ceramic material such as zirconium oxide. The first unit can be arranged in tubes that can be attached to each other in an end-to-end manner. For example, the first unit can be arranged short tubes which can be assigned to dental bridges, individual teeth, etc., or in longer tubes in which one or more ceramic material rods can be adhesively bonded. The ceramic materials can be preferably assigned a cylindrical shape.

In accordance with another embodiment, an arrangement can be configured such that the ceramic material can be surrounded by the second or enclosure unit to which it is secured via its outer surface or outer surfaces. Further, the enclosure unit can be designed so that it can be fed forward and divided. The enclosure unit and the material lying inside it in the respective part can be arranged, on the one hand, for silhouetting which extends completely or partially in both the ceramic material and the surrounding material, and, on the other hand, for leaving securing parts between the materials.

The arrangement can preferably be configured such that the second unit is made of a select material essentially different than the material of the first unit. Further, the securing part can comprise one of a combination of the material of the second unit with a joining material and a combination of the material of the first unit with the joining material.

By means of what has been proposed above, the ceramic blank or the material can be produced by isostatic pressing. To obtain blanks which are as homogeneous and gradient-free as possible, the blanks can be assigned a cylindrical shape. The blank or the material can be adhesively bonded into a tubular holder which is made of a stiff and durable material that can be easy to machine. During machining, such as milling, of the dental products in question, so-called silhouette milling can be applied. By virtue of the arrangement, the silhouetted ceramic material can be provided with a holding part or frame of less expensive material.

In accordance with an embodiment of the tube method, the tube, together with the glue that holds the blank firmly in the tube, can form the frame after and during the machining. The blank in the frame can be made of plastic or aluminum which can be considerably less expensive than the chosen ceramic material, and this in itself can constitute a substantial cost saving. In accordance with another embodiment, it is also possible to provide short tubes for a bridge or long tubes with one or more zirconium oxide rods adhesively bonded in them. The long tubes can provide the great advantage that the advancing mechanism known in today's machining devices can be used. In this regard, it can be possible to eliminate manual assembly of the ceramic blank or the material. Therefore, highly efficient production installations can be set up without components having to be handled by means of costly robotic charging.

BRIEF DESCRIPTION OF THE DRAWINGS

The abovementioned and other features of the inventions disclosed herein are described below with reference to the drawings of the preferred embodiments. The illustrated embodiments are intended to illustrate, but not to limit the inventions. The drawings contain the following figures:

FIG. 3 shows a longitudinal sectional view taken along section lines A-A of FIG. 2 illustrating the tube and the ceramic blank.

FIG. 4 shows a perspective view, obliquely from above, of an advancing mechanism for a tube with ceramic material lying inside it, arranged on a CAD appliance, according to another embodiment.

DETAILED DESCRIPTION OF THE PREFERRED EMBODIMENT

Figure 2:
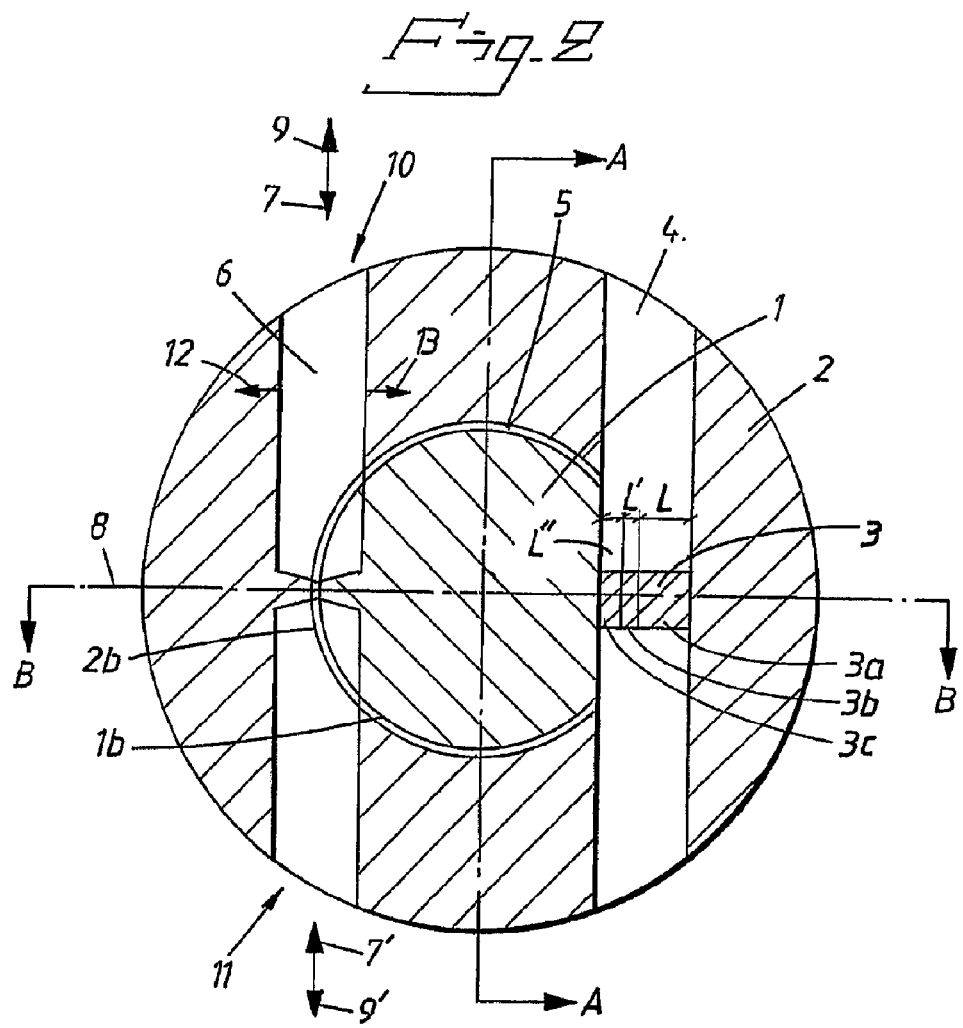
FIG. 2 is a cross sectional view showing a tube and a ceramic material lying inside it, as well as a silhouetting function which can be performed from two opposite directions.
Figure 1:
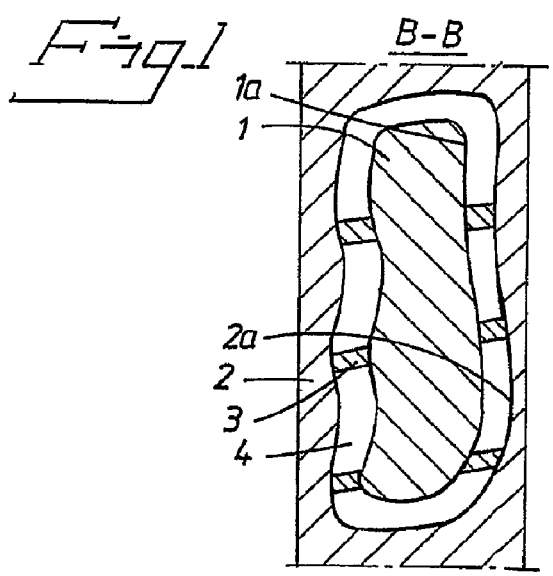
FIG. 1 shows a horizontal cross sectional view taken along section lines B-B of FIG. 2 illustrating an embodiment wherein silhouetting is being carried out on a tubular part with a ceramic blank placed inside it according to an embodiment.

FIGS. 1-3 illustrate various views of an embodiment of the present inventions. FIG. 1 illustrates a first unit 1 and a second unit 2 that can be configured to surround the first unit 1. The first and second units 1, 2 can be joined by securing parts 3 which can extend from the first unit 1 outward to the second unit 2.

The first unit 1 can be made of ceramic material. The ceramic material can consist of zirconium oxide and the second part can be made of aluminum, a dimensionally stable plastic, or another material which can be less expensive than the ceramic material. The material of the first unit 1 and that of the second unit 2 can be subjected to silhouetting. As a result, the first unit 1 can have an outer silhouette 1a and the second unit 2 can have an inner silhouette 2a. The silhouetting can be performed by milling from two opposite directions. One direction can be a direction substantially perpendicular to the plane of the figure in FIG. 1, while the other direction is a direction extending from under the view shown in FIG. 1 and upward at right angles to the plane of the figure. As illustrated in FIG. 1, the silhouetting can be carried out such that said securing parts 3 have been left. The silhouetting can depend on the shape which the ceramic material is to be given, and, similarly, the number and formation of the securing parts 3 can depend on the securing wanted for the first unit 1 with respect to the second unit 2. The actual silhouetting is indicated by 4 in FIG. 1.

Referring now to FIG. 2, the second unit 2 can be formed in a tubular configuration. In the cross sectional view shown in FIG. 2, the first unit 1 in the initial stage can have the shape of a cylindrical rod or part which extends at right angles to the plane of the figure in FIG. 2. The tube (i.e. the second unit 2) and the cylindrical part (i.e. the first unit 1) can be joined to one another by a layer of glue 5. The layer of glue can thus connect the outer surface 1b of the first part 1 and the inner surface 2b of the tube. The figure shows a member which can effect the silhouetting and which, in the present illustrative embodiment, can be in the form of milling equipment.

The actuating part 6 of the milling tool carrying out the milling can be fed in two opposite directions during the silhouetting. In a first stage, the actuating part 6 can be driven into the material of the tube and of the first unit 1 in a first direction which is indicated by a directional arrow 7. The actuating part 6 can be driven down to the center line 8 which is substantially at right angles to the first direction of movement 7, which direction of movement coincides with the plane of the figure in FIG. 2. When the upper half of the tube and of the cylindrical part has thus been milled, the actuating part 6 can be moved in a direction of withdrawal which is indicated by 9. A first milling direction is symbolized by 10 in FIG. 2.

The second half of the milling or silhouetting takes place from an opposite direction which is symbolized by 11 in FIG. 2. In this case, the directions of movement are indicated by arrows 7' and 9'. These opposite directions are at substantially 180° to one another. The milling from underneath can take place in a corresponding manner up to the diameter line 8 in FIG. 2.

The milling function can result in what in principle is a continuous silhouette groove 4, except for the securing parts 3 which are left during the silhouetting or milling. In an alternative embodiment, only one direction 10 or 11 is used, in which case the first and second units can be turned or rotated 180° about their longitudinal axis between the two milling steps.

According to some embodiments, the milling can be performed at the transition between the first and second units and the layer of glue 5. Depending on the extent of the silhouetting, the securing parts 3 can be made of different material compositions. Preferably, most or all of the securing parts 3 can be formed from the material of the tube shape and of the layer of glue 5. Alternately, a certain length can consist of the material of the first unit 1. Lengths L, L' and L" have been indicated in FIG. 2, and it is advantageous here that the distances L and L' take up the greater part of the length of the securing part, for example at least 90° of the part. In FIG. 2, the milling needle directions have been indicated in relation to the first and second material 1, 2 and the layer of glue 5 and, during silhouetting, the actuating part 6 of the milling tool can be moved in the directions of the arrows 12 and 13 in order to create a curved silhouette 1a (illustrated in FIG. 1).

FIG. 3 is a side cross sectional view along the section lines A-A of FIG. 2. As shown in FIG. 3, the thickness of the layer of glue 5 is indicated by H. The thickness can be chosen preferably between 0.5 and 1 mm. The external and internal diameters D and d, respectively, of the tube 2 can be chosen as a function of the strength which is desired to be obtained for the rod or rod part in its entirety. The dimensions of the cylindrical part 1 can be also chosen in relation to the product which is to be handled and machined. The glue 5 can be a conventional glue or, alternately, a curable polymer.

In accordance the embodiment illustrated in FIG. 4, a tube 2' can be advanced in an advancing device 14, which can form part of a CAD appliance. The tube 2' can comprise a number of cylindrical first units 1', 1", 1''', etc. Alternately, said first units can form a common cylinder-shaped unit which can be divided in cutting equipment (not shown specifically).

In FIG. 4, a milling drill is indicated by 15. The second unit 2', with the first unit or units inside it, can be advanced in the direction 16 and the milling can be carried out by the milling tool 15 in both directions 10' and 11' (cf. above). In this embodiment, the tube can thus be turned or rotated 180° in relation to the dividing line 17 during the silhouetting. Less ceramic material can be used up, and the securing parts are stronger since the ceramic material itself does not have to form the securing parts. Further, the securing parts to a large extent can comprise the materials in the second unit 2' and the glue connection.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

The invention claimed is:

1. A method for forming a product for the production of a dental prosthesis, the method comprising:
providing the product comprising a first unit made of a first material and a second unit made of a second material that is different than the first material, the first unit being at least partially enclosed by the second unit and secured to an inner surface of the second unit with a joining material; and
removing a portion of the product from two directions to form a silhouette at a transition between the first and second units, the silhouette defining an outer silhouette surface that faces an inner silhouette surface and sections that extend between the inner and outer silhouette surfaces to secure the first unit to the second unit,
wherein said sections comprise the joining material and the second material,
wherein removing a portion of the product from two opposite directions to form a silhouette at a transition between the first and second units includes subjecting the first material of the first unit and the second material of the second unit to silhouetting, and
wherein at least a portion of the first material and the second material are removed during silhouetting.

2. The method of claim 1, further comprising forming the inner silhouette surface substantially on the second unit.

3. The method of claim 1, further comprising forming the outer silhouette surface substantially on the first unit.

4. The method of claim 1, wherein removing a portion of the product comprises milling.

5. The method of claim 1, wherein removing a portion of the product from two opposite directions comprises rotating the product.

6. The method of claim 5, wherein rotating the product comprises rotating the product about 180 degrees.

7. The method of claim 1, wherein removing a portion of the product comprises advancing a tool from two opposite directions.

8. The method of claim 1, further comprising cutting the product into smaller segments.

9. The method of claim 1 wherein the step of removing a portion of the product comprises removing the product from two opposite directions to form the silhouette at a transition between the first and second units.

10. The method of claim 1 wherein said sections comprise the joining material, the second material, and the first material.

11. A method for forming a product for the production of a dental prosthesis, the method comprising:
providing the product comprising a first unit made of a first material and a second unit made of a second material that is different than the first material, the first unit being at least partially enclosed by the second unit and secured to an inner surface of the second unit with a joining material; and
removing at least a portion of the first and second materials of the product to form a silhouette at a transition between the first and second units, the silhouette defining an outer silhouette surface that faces an inner silhouette surface and securing parts that extend between the inner and outer silhouette surfaces to secure the first unit to the second unit, said securing parts comprising the joining material and the second material.

12. The method of claim 11 wherein the step of removing a portion of the product comprises removing the product from two opposite directions to form the silhouette at a transition between the first and second units.

13. The method of claim 11 wherein said sections comprise the joining material, the second material, and the first material.

14. The method of claim 11 further comprising forming the inner silhouette surface substantially on the second unit.

15. The method of claim 11 further comprising forming the outer silhouette surface substantially on the first unit.

16. The method of claim 11 wherein removing a portion of the product comprises milling.

* * * * *